US012655740B2

(12) United States Patent
Detweiler et al.

(10) Patent No.: US 12,655,740 B2
(45) Date of Patent: Jun. 16, 2026

(54) SENSOR EMPLACEMENT USING UNMANNED AIRCRAFT SYSTEMS

(71) Applicant: NUtech Ventures, Lincoln, NE (US)

(72) Inventors: Carrick Detweiler, Lincoln, NE (US); Brittany Anne Duncan, Lincoln, NE (US); Justin Mathew Bradley, Lincoln, NE (US); Jacob Hogberg, Lincoln, NE (US); Paul Adam Plowcha, Papillion, NE (US)

(73) Assignee: NUtech Ventures, Lincoln, NE (US)

( * ) Notice: Subject to any disclaimer, the term of this patent is extended or adjusted under 35 U.S.C. 154(b) by 305 days.

(21) Appl. No.: 18/127,046

(22) Filed: Mar. 28, 2023

(65) Prior Publication Data

US 2024/0352842 A1 Oct. 24, 2024

Related U.S. Application Data

(60) Provisional application No. 63/324,355, filed on Mar. 28, 2022.

(51) Int. Cl.
*E21B 44/00* (2006.01)
*B64U 20/00* (2023.01)
(Continued)

(52) U.S. Cl.
CPC .............. *E21B 44/00* (2013.01); *B64U 20/00* (2023.01); *G01N 33/24* (2013.01); *B64U 2101/00* (2023.01)

(58) Field of Classification Search
CPC ..... E21B 44/00; B64U 20/00; B64U 2101/00; G01N 33/24
(Continued)

(56) References Cited

U.S. PATENT DOCUMENTS 4,332,160 A * 6/1982 Baragar ................. G01N 33/24
73/84
5,182,731 A * 1/1993 Hoelscher ............... E21B 47/20
367/84
(Continued)

FOREIGN PATENT DOCUMENTS

CN 207943163 U * 10/2018
DE 202017003305 U1 * 11/2018 ........... E21B 1/0021

OTHER PUBLICATIONS

Quan, Qiquan et al. "Drilling Load Modeling and Validation Based on the Filling Rate of Auger Flute in Planetary Sampling." Chinese journal of aeronautics 30.1 (2017): 434-446. Web. (Year: 2017).*

*Primary Examiner* — Donald J Wallace
*Assistant Examiner* — Keith A Von Volkenburg
(74) *Attorney, Agent, or Firm* — Sage Patent Group

(57) ABSTRACT

Systems and methods for sensor emplacement using unmanned aircraft systems (UASs). In some examples, a UAS includes a propulsion system and a sensor emplacement system including an auger and one or more motors. The UAS includes a control system configuring for controlling the propulsion system to land the UAS at a sensor emplacement site and controlling the one or more motors of the sensor emplacement system to drive the auger into soil at the sensor emplacement site. The control system is configured for measuring one or more augering parameters from the sensor emplacement system; and determining, using an autonomous system trained on soil data and augering data, one or more soil classification values for the soil based on the one or more augering parameters.

23 Claims, 10 Drawing Sheets

(51) Int. Cl.
    *G01N 33/24*       (2006.01)
    *B64U 101/00*     (2023.01)

(58) Field of Classification Search
    USPC ........................................................ 701/16
    See application file for complete search history.

(56)                  References Cited

U.S. PATENT DOCUMENTS

| | | | |
|---|---|---|---|
| 6,116,819 A * | 9/2000 | England | E21B 44/00 |
| | | | 405/233 |
| 6,651,755 B1 * | 11/2003 | Kelpe | E21B 44/00 |
| | | | 175/45 |
| 11,079,725 B2 * | 8/2021 | Palla | G05B 13/048 |
| 2003/0044241 A1 * | 3/2003 | Mure | E02D 33/00 |
| | | | 405/231 |
| 2018/0080311 A1 * | 3/2018 | Daubner | E02F 3/22 |
| 2019/0265015 A1 * | 8/2019 | Michiwaki | G01B 7/16 |
| 2020/0150067 A1 * | 5/2020 | Ruys | G01N 33/246 |
| 2020/0193589 A1 * | 6/2020 | Peshlov | G06V 20/188 |
| 2020/0255139 A1 * | 8/2020 | Nahuel-Andrejuk | |
| | | | G01D 21/02 |
| 2020/0255140 A1 * | 8/2020 | Nahuel-Andrejuk | |
| | | | G05D 1/0094 |
| 2020/0257318 A1 * | 8/2020 | Nahuel-Andrejuk | |
| | | | G05D 1/0094 |
| 2021/0103728 A1 * | 4/2021 | Young | G06V 20/56 |
| 2022/0067121 A1 * | 3/2022 | Huber | A01B 79/005 |
| 2022/0365007 A1 * | 11/2022 | Huang | G01N 23/223 |

\* cited by examiner

Figure 3B:
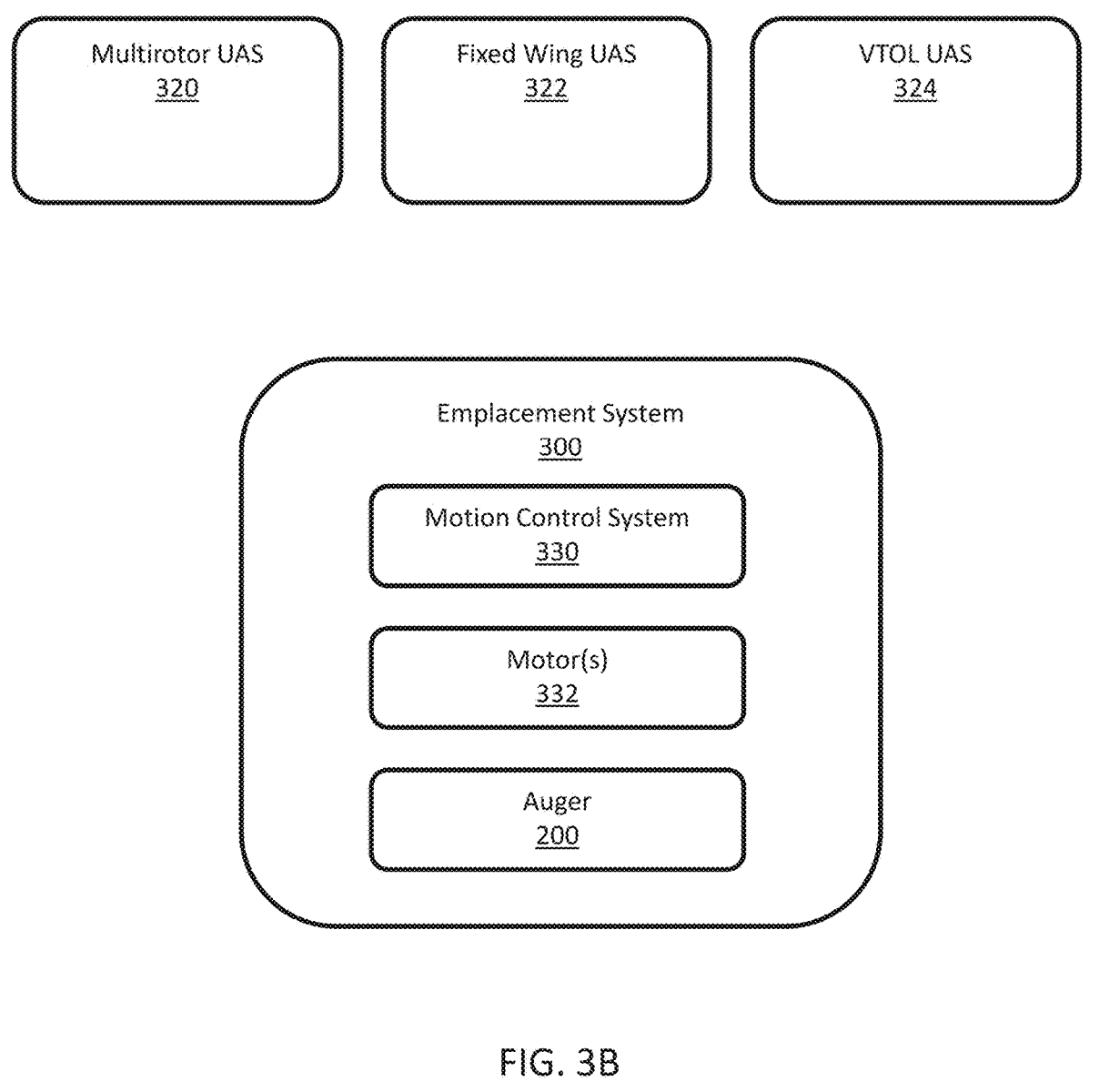

Multirotor UAS
320

Fixed Wing UAS
322

VTOL UAS
324

Emplacement System
300

Motion Control System
330

Motor(s)
332

Auger
200

Deploy UAS to emplacement site
602

Initiate sensor emplacement
604

Measure auguring parameter(s)
606

Determine soil condition(s) using trained classifier
608

900

Deploy UAS to emplacement site
902

Initiate sensor emplacement
904

Determine soil classification values
906

Determine probability of success
908

Probability greater than threshold?
910

Yes

No

Try alternate site or end mission
912

SENSOR EMPLACEMENT USING UNMANNED AIRCRAFT SYSTEMS

CROSS-REFERENCE TO RELATED APPLICATIONS

This application claims benefit of U.S. Provisional Application Ser. No. 63/324,355, filed on Mar. 28, 2022, the disclosure of which is incorporated herein by reference in its entirety.

GOVERNMENT INTEREST

This invention was made with government support under 17-FU903-00, 18-FU914-00, 18-FU914-01, 18-FU914-02, 18-FU914-04, and 17-FU903-01 awarded by the National Strategic Research Institute and under U.S. Pat. No. 1,925, 368 awarded by the National Science Foundation. The government has certain rights in the invention.

BACKGROUND

The subject matter described in this specifically relates generally to sensor emplacement using unmanned aircraft systems (UASs), e.g., autonomous in-ground sensor emplacement using UASs.

Remote deployment of sensors in hard-to-access locations can enable improved data gathering for scientific study. Some sensors, such as seismic or soil moisture sensors, function best when placed into the soil, although the composition of the soil may be unknown. Some conventional systems use machine learning in the analysis of soil composition. In these conventional systems, however, measuring the parameters to be used in a soil composition prediction scheme make use of either equipment or facilities not available for a UAS-sized platform. Additionally, these methods often require the sampling and removal of material from the environment. The material is analyzed external to the device.

SUMMARY

This document describes a sensor emplacement system that can be mounted to unmanned aircraft systems to autonomously auger a sensor into the ground. Various techniques can be chosen to enhance the augering process when certain characteristics of the soil are known. Moisture content and compressive strength are the soil characteristics that most impact the augering process, yet directly measuring them would require additional sensors to an already-burdened airframe. The system and methods described in this document can determine soil characteristics using sensors internal to the sensor emplacement system during the physical act of drilling into the soil.

BRIEF DESCRIPTION OF THE DRAWINGS

FIG. 3B is a block diagram illustrating the modular nature of the sensor emplacement system;

DETAILED DESCRIPTION

This document describes an in-ground sensor emplacement system for an unmanned aircraft system (UAS) capable of remotely augering sensors into the soil. In general, the UAS arrives in the area where the sensor is to be placed and lands. It then uses an augering mechanism to drill a sensor into the ground. If the system cannot successfully emplace the sensor into the ground, then it relocates to a new location and tries again. If sensor emplacement is successful, then the UAS departs the area.

Figure 1:
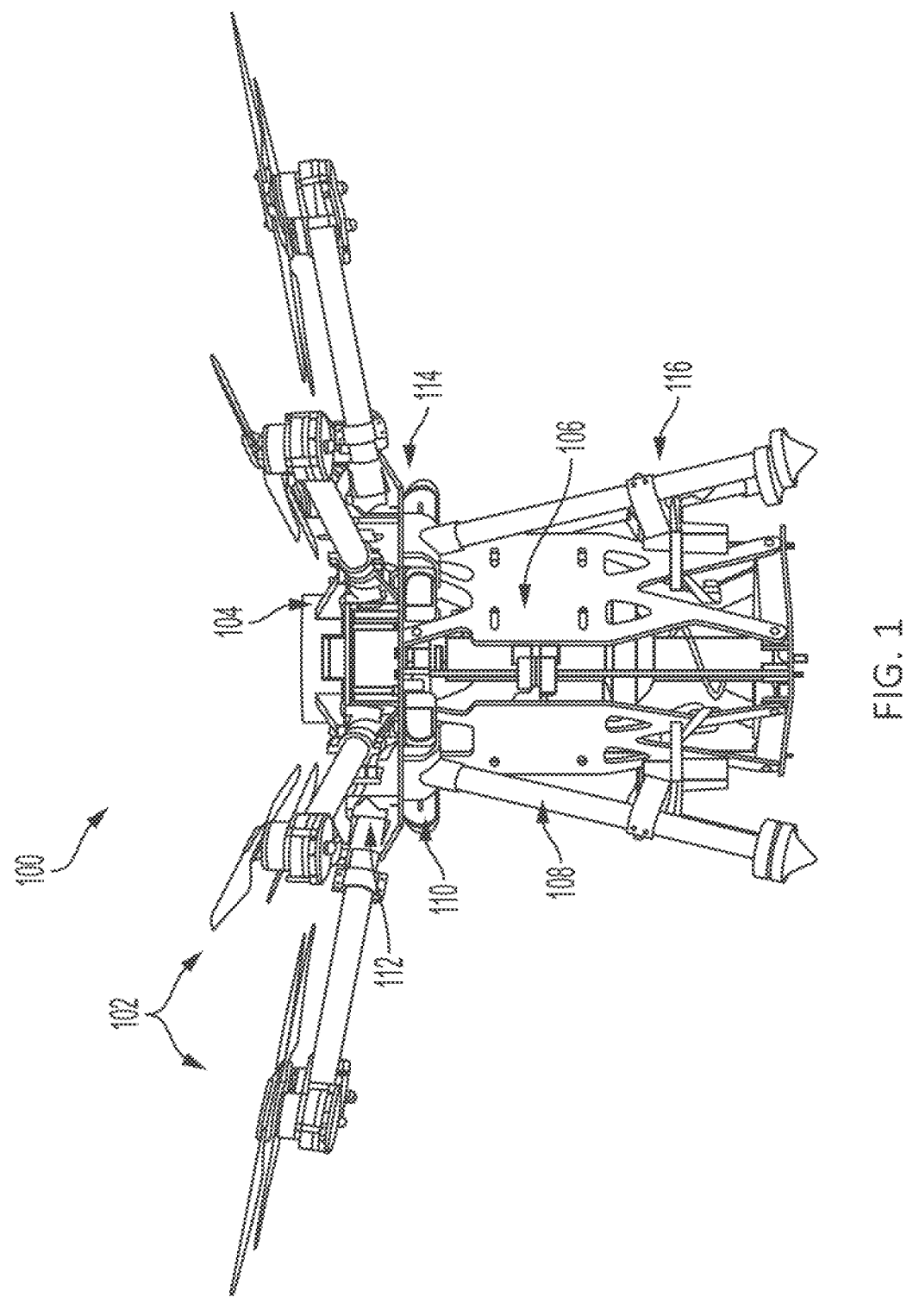
FIG. 1 shows an example UAS.

FIG. 1 shows an example UAS 100. The UAS 100 is a multicopter having a propulsion system 102 with a number of rotating blades. The UAS 100 is shown as an example of a UAS that can use an in-ground sensor emplacement system as described in this document; however, in general, the sensor emplacement systems can be used with any appropriate type of UAS.

The UAS 100 includes a flight controller 104, a sensor emplacement system 106 for digging an auger into the ground, and landing gear 108. The landing gear 108 can include a number of stationary legs with conically spiked feet that penetrate the ground and aid with anchoring the UAS 100 in place during auger operations. In some examples, the UAS 100 includes a fuselage baseplate 110, motor arm mounts 112, motor arm springs 114, and motor arm releases 116 to allow the UAS 100 to collapse, e.g., for transport and storage. The UAS 100 can be implemented, for example, on a DJI S-1000 outfitted with the open source hardware Pixhawk flight controller running the open source ArduPilot Mega flight control firmware stack.

The sensor emplacement system 106 controls the auger's vertical position in the soil column and the downforce on bit by an elevator platform that allows for rapid up and down movement, enabling a technique known as "pecking". The upward movement of the pecking motion allows soil that has been broken up and potentially clogging the lower portions of the auger flutes to be transported up and out of the hole. This creates space for the soil in the bottom of the hole to move into the newly vacant flute areas when the auger is pushed back down into the hole. Soil parameters determine the choice of an effective pecking profile, which can include, e.g., the speed, frequency, and distance of the peck.

Augering and, if necessary, relocating to a new location place considerable demand on the available energy stored in the system's batteries. Therefore, efficiently emplacing the sensor or rapidly determining that a new a location must be tried are two key factors in the overall success of the system. Emplacing the sensor as fast as possible and with the greatest chance of success can be enabled by continuous adjustment of the auger's rotational speed, downward force, and pecking motions but is highly dependent upon key soil parameters (e.g., water content). As a result, knowledge of soil parameters, especially during augering activities, greatly increases the chance of a fast and successful sensor emplacement or determination of imminent failure.

Soil classification covers a wide range of parameters, however, for the purposes of in-ground sensor emplacement to 150 mm, water content and soil compressive strength are the characteristics that can greatly impact the chance of successful emplacement. These key characteristics help determine how much downforce, torque, and speed to apply, whether or not to engage higher level augering strategies (e.g., pecking), and predict whether or not the current digging effort will be successful. However, direct measurement of these parameters is difficult and would require additional equipment to be mounted to the UAS, which may not be possible for some size, weight, and power restrictions. As a result, the system is configured to use, e.g., auger RPM, motor current use, downward force on the auger, and system vibration levels on the UAS 100, alongside a trained autonomous system (e.g., a classifier or other appropriate machine learning model) to determine the water content and compressive strength of the soil.

The on-board sensors used to classify a soil in terms of its water content and compressive strength are not the respective purpose-built moisture sensors and penetrometers, but rather the sensors used for monitoring the system performance of the auger mechanism: auger motor RPM, auger motor current use, weight on auger bit, system vibration (via accelerometers), and time. The data from these sensors is analyzed using machine learning techniques such as decision trees, linear discriminant analysis, naïve Bayesian analysis, k-nearest neighbor (knn) analysis, and Gaussian process regression.

These techniques were evaluated, with a prototype system, in assessing the soil composition within the first 30 seconds of an emplacement operation. Barring any stoppages of the emplacement process, it can take a minimum of 60 seconds to emplace a sensor. This minimum time is increased with an increase in sensor (and subsequent auger) size. The evaluation showed that, in some cases, Gaussian process regression outperforms the other methods at the 30 second mark with an overall average predictive accuracy of 86.53% when determining moisture content and 90.53% when determining soil compressive strength.

The examples described in this document show the UAS 100 drilling into soil and emplacing sensors into soil; however, the UAS 100 can be modified for emplacing sensors into any appropriate material. For example, the autonomous systems of the UAS 100 can be trained using training data from digging into various other surfaces or types of material. The autonomous systems can be trained, for example, for emplacing sensors into wood, metal, concrete, and ice, by collecting training data from prototype systems drilling into these materials and then supplying the training data to machine learning algorithms.

Figure 2:
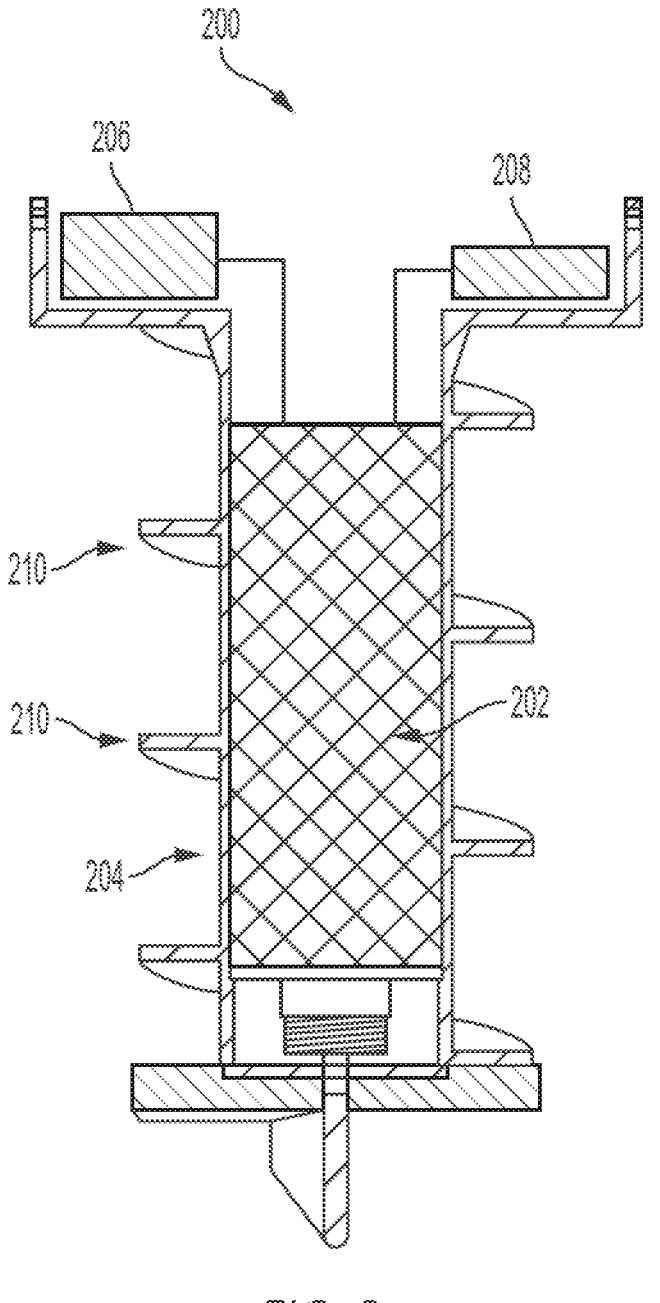
FIG. 2 shows an example sensor housed inside the body of an auger.

FIG. 2 shows an example sensor 202 housed inside the body of an auger 200 which is left behind at the completion of the emplacement sequence. The auger 200 can be any appropriate size, e.g., 150 mm long with a diameter of 75 mm. The term "auger" as used in this document is meant to refer to any kind of auger, drill, or other appropriate device for digging. The auger 200 can be, in general, any of various tools or devices with a shaft or part (e.g., a helical shaft) that are used for boring holes (as in wood, soil, or ice) or moving loose material (such as snow).

The sensor 202 can be any appropriate device that can fit inside the auger 200, for example, within a 100 mm long by 35 mm diameter hollow section of the auger body 204. The sensor 202 can be coupled to a sensor power supply 206 (e.g., a battery) and a sensor antenna 208, such that the sensor 202 can be configured to transmit measurements to a remote system. The auger 200 includes a number of flutes 210 for digging into the ground.

Figure 3A:
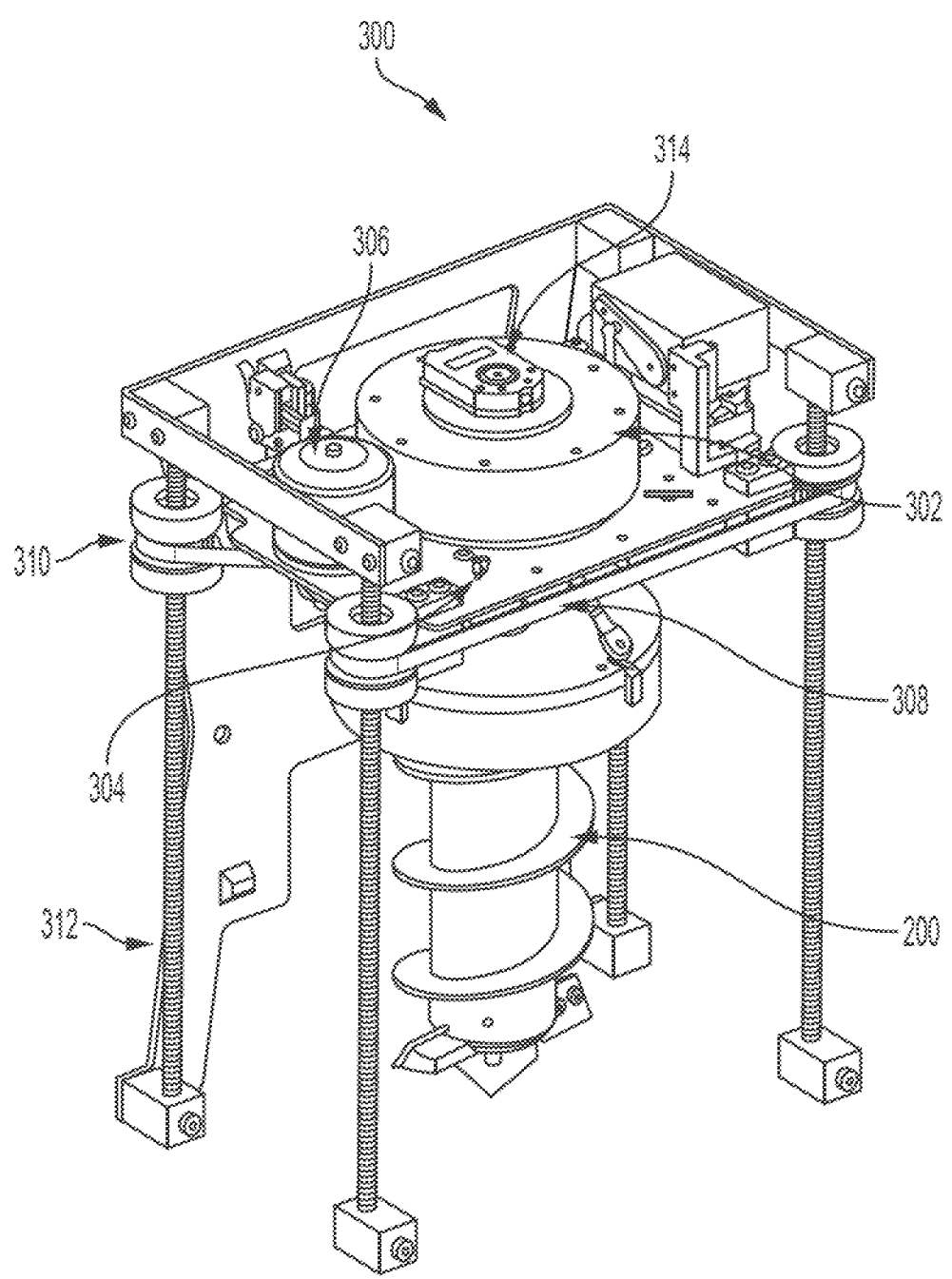
FIG. 3A is a diagram of an example sensor emplacement system.

FIG. 3A is a diagram of an example sensor emplacement system 300. The sensor emplacement system 300 is configured for driving the auger 200 into the ground.

The sensor emplacement system 300 includes an auger motor 302 configured to rotate the auger 200. The auger motor 302 can be, e.g., a T-Motor A80-6 24 volt brushless motor with an integral planetary gear transmission and rotary encoder used for measuring auger RPM.

In some examples, during augering operations, a proportional control law is used to maintain auger rotational speed, e.g., at 200 RPM. In difficult soil conditions where maintaining 200 RPM causes excessive current draw, auger RPM is allowed to decrease in order to maintain safe operating conditions for the auger motor. The auger motor 302 is capable of outputting, e.g., continuous 6 Nm of torque under a 12A load or any appropriate torque. The motor/auger combination is mounted, for example, to an aluminum plate that advances downward during augering operations, e.g., at a rate of 0.1375 cm/s or any appropriate rate.

The sensor emplacement system 300 can include one or more strain gauges 304 mounted to the elevator plate to measure vertical force applied during augering. An inertial measurement unit (IMU) mounted to the aluminum plate can provide data for vibration analysis.

The elevator system includes an elevator motor 306, for example, a smaller T-Motor MN3520 brushless motor, driving a belt 308 connected to pulleys 310 on each corner of the aluminum plate to raise or lower the aluminum platform on four lead screws 312. A rotary encoder 314 is calibrated to measure the vertical distance the platform travels.

FIG. 3B is a block diagram illustrating the modular nature of the sensor emplacement system 300. The sensor emplacement system 300 can be made into a modular design that can be mounted to the underside of various unmanned aircraft systems, e.g., those that have vertical takeoff and landing capability. As shown in FIG. 3B, the system 300 can be mounted on a multirotor UAS 320, a fixed wing UAS 322, or a vertical takeoff and landing UAS 324.

The system 300 can be housed in an aluminum chassis that can be adapted to fit on any applicable air frame. In some cases, an appropriate air frame is capable of operating with a 2.7 kg payload and supplying the system 300 with 24 volts DC.

As shown in FIG. 3B, the system 300 includes a motion control system 330, one or more motors 332 (e.g., the auger motor 302 and the elevator motor 306), and the auger 200. The motion control system 330 can be implemented using any appropriate combination of electronics. In some examples, the motion control system 330 includes an Odrive Robotics motor controller to control the auger motor 302 and elevator motor 306, while an ATMega-based microcontroller is used as the primary computing device that manages communications with the Odrive controller and outputs the various measured parameters via serial connection.

The system 300 can, in general, include any appropriate sensors. For example, the system 300 can include a soil moisture sensor, a seismic sensor, one or more cameras (e.g., visual or thermal), or a conductivity sensor. The motion control system 330 can receive signals from these sensors and use the signals (e.g., in addition to monitoring motors) to determine appropriate control of the motors 332.

Figure 4:
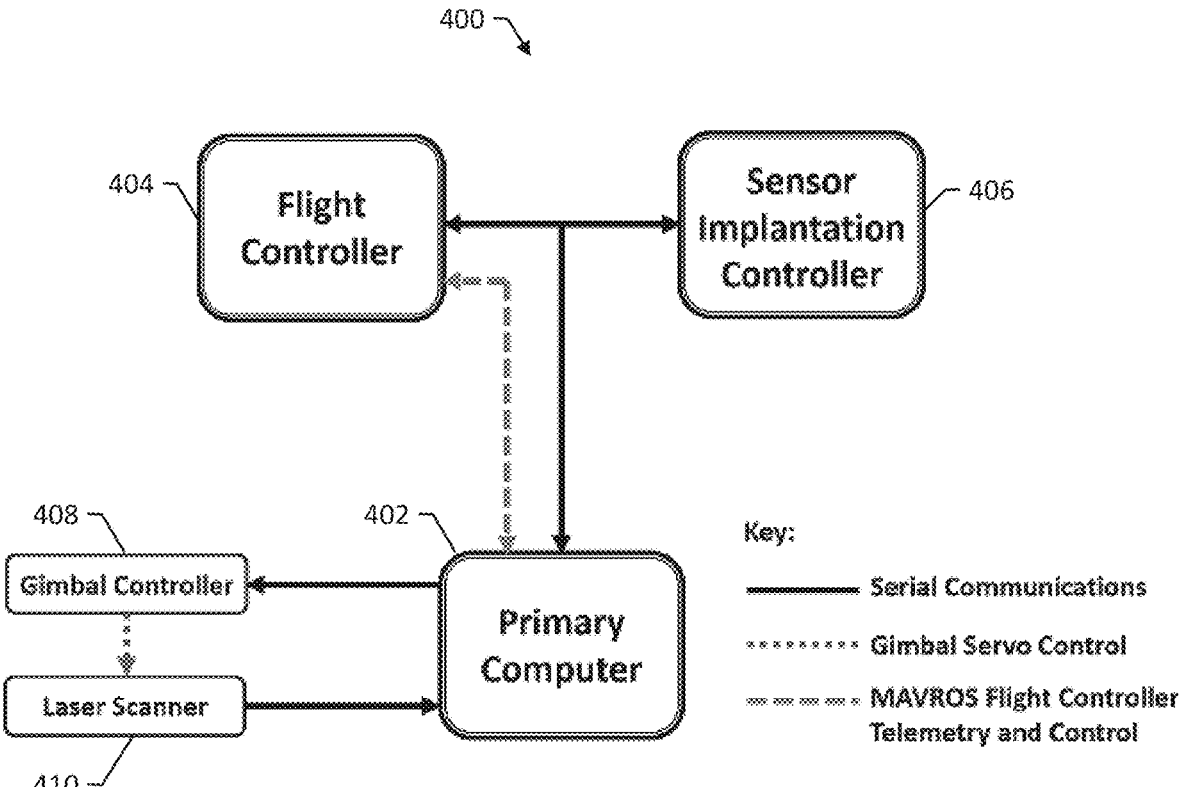
FIG. 4 is a block diagram of an example control system for a UAS having a sensor emplacement system.

FIG. 4 is a block diagram of an example control system 400 for a UAS having a sensor emplacement system. The control system 400 includes a primary computer 402, a flight controller 404, and a sensor emplacement controller 406.

The primary computer 402, flight controller 404, and sensor emplacement controller 406 can communicate, e.g., via a serial communications interface. In some examples, the control system 400 includes a laser scanner landing zone evaluation system, including a gimbal controller 408 and a laser scanner for determining a suitable landing zone.

The primary computer 402 can use, for example, the Robot Operating System's MAVROS package for full-duplex communications with the flight controller 404 via the Micro Air Vehicle Communication Protocol.

Communication between the computational systems occurs as follows. When the UAS reaches the programmed sensor emplacement location, the flight controller 404 signals the primary computer 402 to scan the landing zone. The flight controller 404 waits for the scanning operation to complete and the primary computer 402 to command either a landing, if the landing zone is suitable, or flight to a new location, if it is not.

Once a landing is complete, the flight controller 404 then commands the sensor emplacement controller 406 to commence emplacement operations. Depending on the outcome of the emplacement operation, one of two actions are performed. If sensor emplacement is successful, the auger/sensor housing is released from the motor, the sensor emplacement controller 406 signals success to the flight controller 404 which then launches the UAS and flies to a predetermined scuttle location. If sensor emplacement fails, the sensor emplacement controller 406 retracts the auger/sensor housing, signals failure to the primary computer 402 which then computes and loads the next potential sensor emplacement location into the flight controller 404. Once the flight controller 404 receives this new flight plan, it launches the UAS and proceeds to the next potential emplacement area and begins the landing zone selection and verification process over again.

Figure 5:
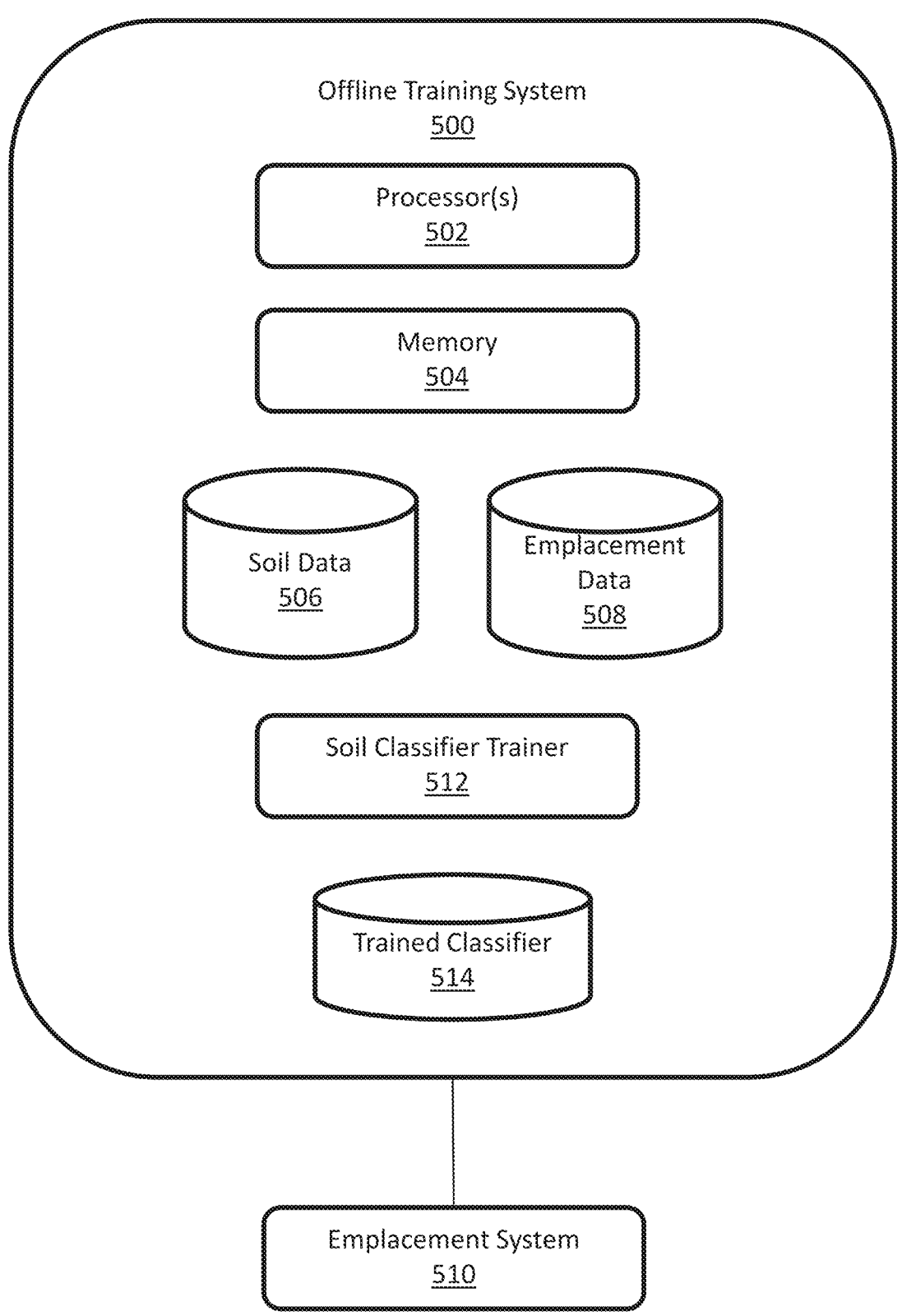
FIG. 5 is a block diagram of an example offline training system.

FIG. 5 is a block diagram of an example offline training system 500. The offline training system 500 includes at least one processor 502 and memory 504 storing instructions for the processor 502.

The offline training system 500 receives soil data 506 and emplacement data 508 from at least one emplacement system 510. The soil data 506 and emplacement data 508 can be gathered in any appropriate way, e.g., by moving the emplacement system 510 to various sites, measuring emplacement data 508 during an emplacement operation, and then measuring the soil characteristics to obtain truth data. The soil data 506 includes, for each of a number of locations, the measured soil characteristics values. The emplacement data 508 includes, for each location, the measured emplacement values.

The emplacement data 508 can include augering parameters, for example:

Revolutions per minute of the auger motor—measured in RPM

Current draw of the auger motor—measured in Amps

Weight on auger bit (WOB)—measured by the strain gauges in kg

Elevator position relative to top—measured in cm.

Acceleration in the X, Y, and Z axes—measured in $m/s^2$

Time—each line of logged output is timestamped in seconds

The soil data 506 can include any appropriate values characterizing the soil. Soil can be described by various parameters ranging from its particle sizes to its organic material content. Higher moisture content and/or higher compressive strength coincide with a reduced chance of success for an augering evolution. An increase in moisture leads to an increase in friction between the soil and the auger surfaces. Higher compressive strength means the soil is more compact and requires that more force be applied in order to loosen the soil for transport up the auger's flutes.

To obtain truth data, the soil moisture content and soil compressive strength can be manually measured with tools and techniques accepted in the pedology community: a capacitive moisture sensor, volumetric analysis, and penetrometer. Specifically, the percentage of soil moisture can be measured with a capacitive device for each trial, with every tenth trial verifying the moisture content by volumetric means (i.e., weighing the soil before and after baking the moisture out in an oven). Measurements can be taken from the upper, middle, and lower thirds of the soil column at the completion of each augering operation.

The unconfined compressive strength of soil is defined as the amount of force required to crush or displace the soil within a given area and is measured in $kg/cm^2$. The soil can be measured with a penetrometer by probing the side wall of the resultant hole left by the auger. Measurements can be taken near the surface, in the middle third of hole, and at the bottom.

The offline training system 500 includes a soil classifier trainer 502. The soil classifier trainer 502 uses the soil data 506 and the emplacement data 508 to produce an autonomous system, for example, a trained classifier 514 for predicting soil classification values from emplacement data. The soil classifier trainer 502 can use the emplacement data 508 as the predictor variable in any appropriate classification/regression scheme. For example, the soil classifier trainer 502 can use one of the following: decision tree, linear discriminant, naïve Bayes, k-nearest neighbor, and Gaussian process regression. The responses in these schemes are the soil classification values, e.g., soil moisture content and soil compressive strength. In some examples, the soil classifier trainer 502 can use Matlab®'s "fitctree( )," fitcdiscr( )," fittcnb( )," "fitcknn( )," and "fitrgp( )" methods to generate the trained classifier 514.

Since a goal of the system is to determine the soil classification values as quickly as possible, the trained classifier 514 can be evaluated for its predictive accuracy at different time intervals, e.g., at 5, 10, 20, and 30 seconds into an augering evolution. Testing of a prototype showed that it is possible sensor that provide auger RPM, auger motor current, auger depth, weight on bit, and acceleration data. Gaussian process regression generates the most accurate policy of the schemes that were tested. It can predict within the first 30 seconds of an average 85 second augering evolution the soil moisture content within 86.53% of the actual value and soil compressive strength within 90.53% of the actual value.

The trained classifier 514 can then be installed on a production system, e.g., on the emplacement system 510, and used in the field during live operation for sensor emplacement.

In some examples, the system 500 can be configured to produce the trained classifier 514 for sensor emplacement into other materials and locations. In general, the system 500 can produce the trained classifier 514 by training on data from the augering processing and emplacement material. For example, the system 500 can train the classifier 514 using training data from sensor emplacement testing performed on wood, metal, concrete, or ice. The emplacement system 510 can then use the classifier 514 to determine properties of the emplacement material, while augering, and use the determined properties, e.g., to adjust the augering strategy or to predict a likelihood of success for the mission.

7                                                                                 8

Figure 6:
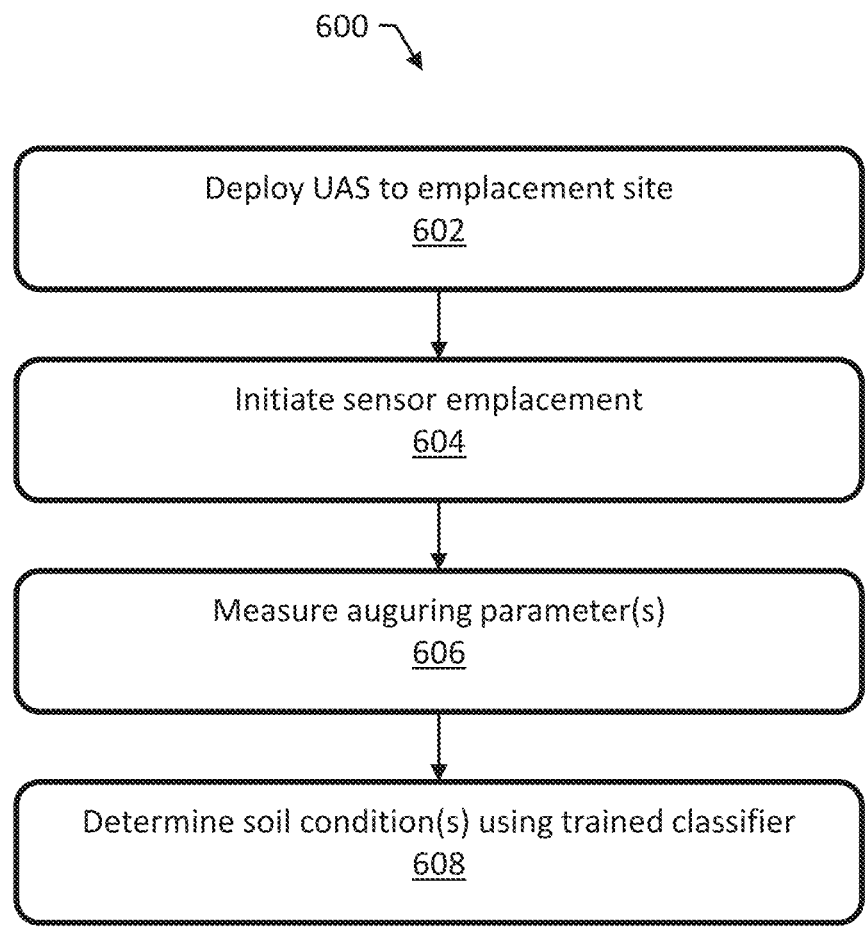
FIG. 6 is a flow diagram of an example method for determining one or more soil classification values.

FIG. 6 is a flow diagram of an example method 600 for determining one or more soil classification values. The method 600 can be performed, for example, by the UAS 100 of FIG. 1 having a sensor emplacement system.

The method 600 includes deploying the UAS by controlling a propulsion system of the UAS to land the UAS at a sensor emplacement site (602). The method 600 includes initiating sensor emplacement by controlling one or more motors of the sensor emplacement system to drive an auger into soil at the sensor emplacement site (604). An example algorithm for sensor emplacement is provided below.

| Algorithms Sensor emplacement |
| --- |
| 1.  procedure EMPLACESENSOR |
| 2.      currentState ← advancing; |
| 3.      while targetDepthAchieved ‖ timeLimitExceeded do |
| 4.          if motorCurrent > currentLimit ‖ shaftRPM < rpmLimit ‖ shaftAdvance == false then |
| 5.              //Pecking maneuver. |
| 6.              currentState ← partialRetraction; ‖ |
| 7.          end if |
| 8.          if targetDepthAchieved then |
| 9.              currentState ← fullRetraction; |
| 10.             return SUCCESSFUL-EMPLACEMENT; |
| 11.         end if |
| 12.         if timeLimitExceeded then |
| 13.             currentState ← fullRetraction; |
| 14.             return FAILED-EMPLACEMENT; |
| 15.         end if |
| 16.     end while |
| 17.  end procedure |

The method 600 includes measuring one or more augering parameters from the sensor emplacement system (606). The one or more augering parameters can include one or more of: revolutions per minute of an auger motor causing the auger to rotate; current draw of the auger motor; weight on auger bit as measured by a strain gauge of the sensor emplacement system; elevator position of an elevator system driving the auger downward into the soil; and acceleration in an X axis, a Y axis, and/or a Z axis, as measured by, e.g., an accelerometer.

The method 600 includes determining, using a classifier trained on soil data and augering data, one or more soil classification values for the soil based on the one or more augering parameters (608). The one or more soil classification values can include one or more of: soil moisture and soil compressive strength. The classifier can be trained on the soil data and augering data using one of the following machine learning models: decision tree; linear discriminant; naïve Bayes; k-nearest neighbor; and Gaussian process.

Figure 7:
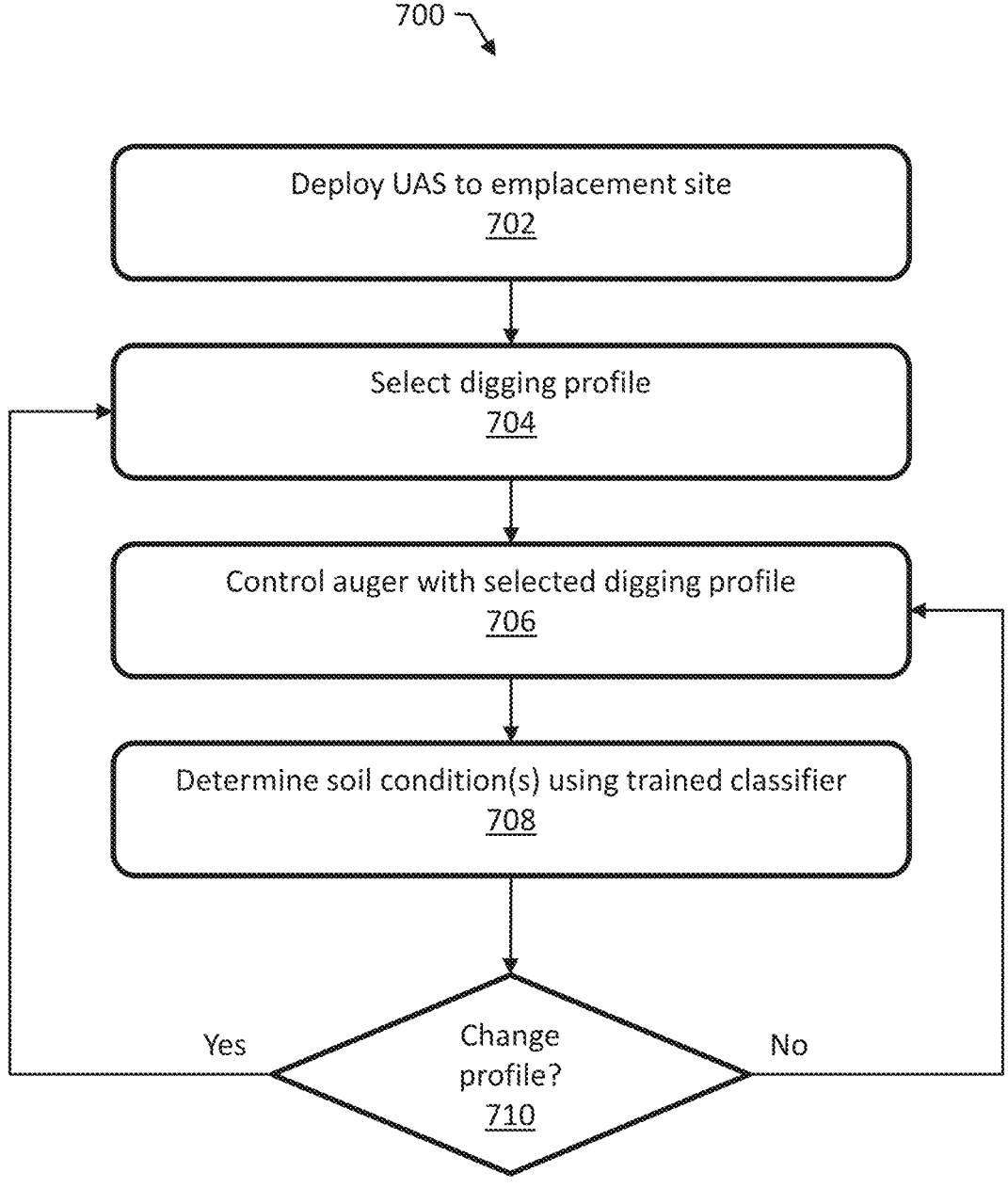
FIG. 7 is a flow diagram of an example method for adaptive auger driving based on soil classification.

FIG. 7 is a flow diagram of an example method 700 for adaptive auger driving based on soil classification. The method 700 can be performed, for example, by the UAS 100 of FIG. 1 having a sensor emplacement system.

The method 700 includes deploying the UAS to a sensor emplacement site (702). The method 700 includes selecting an initial digging profile (704). A digging profile specifies one or more parameters for controlling the auger of the sensor emplacement system, for example, a length of a pecking movement, revolutions per minute of an auger motor causing the auger to rotate, and speed of an elevator system driving the auger downward into the soil. The initial digging profile can be selected, e.g., by selecting a default profile or a default profile based on the sensor emplacement site.

The method 700 includes controlling one or more motors of the sensor emplacement system to drive the auger into the soil as specified in the initial digging profile (706). The method 700 includes measuring one or more augering parameters while driving the auger into the soil and then determining one or more soil classification values based on the augering parameters using a trained classifier (708). For example, the method 700 can including determining the soil classification values after a specified amount of time, e.g., 30 seconds.

The method 700 includes determining whether or not to change the digging profile based on the soil classification values (710). In some examples, each digging profile, of a number of digging profiles, is associated with certain ranges of soil classification values. If a measured soil classification value corresponds to a different digging profile than the initial digging profile, then the method 700 includes determining to change the digging profile (return to 704 and select the different digging profile). Selecting a different digging profile can include, for example, one of: adjusting a length of a pecking movement; slowing revolutions per minute of an auger motor causing the auger to rotate; and slowing a speed of an elevator system driving the auger downward into the soil Otherwise, the method 700 includes continue to drive the auger into the soil until soil emplacement is complete or determining to end the attempted soil emplacement.

Figure 8:
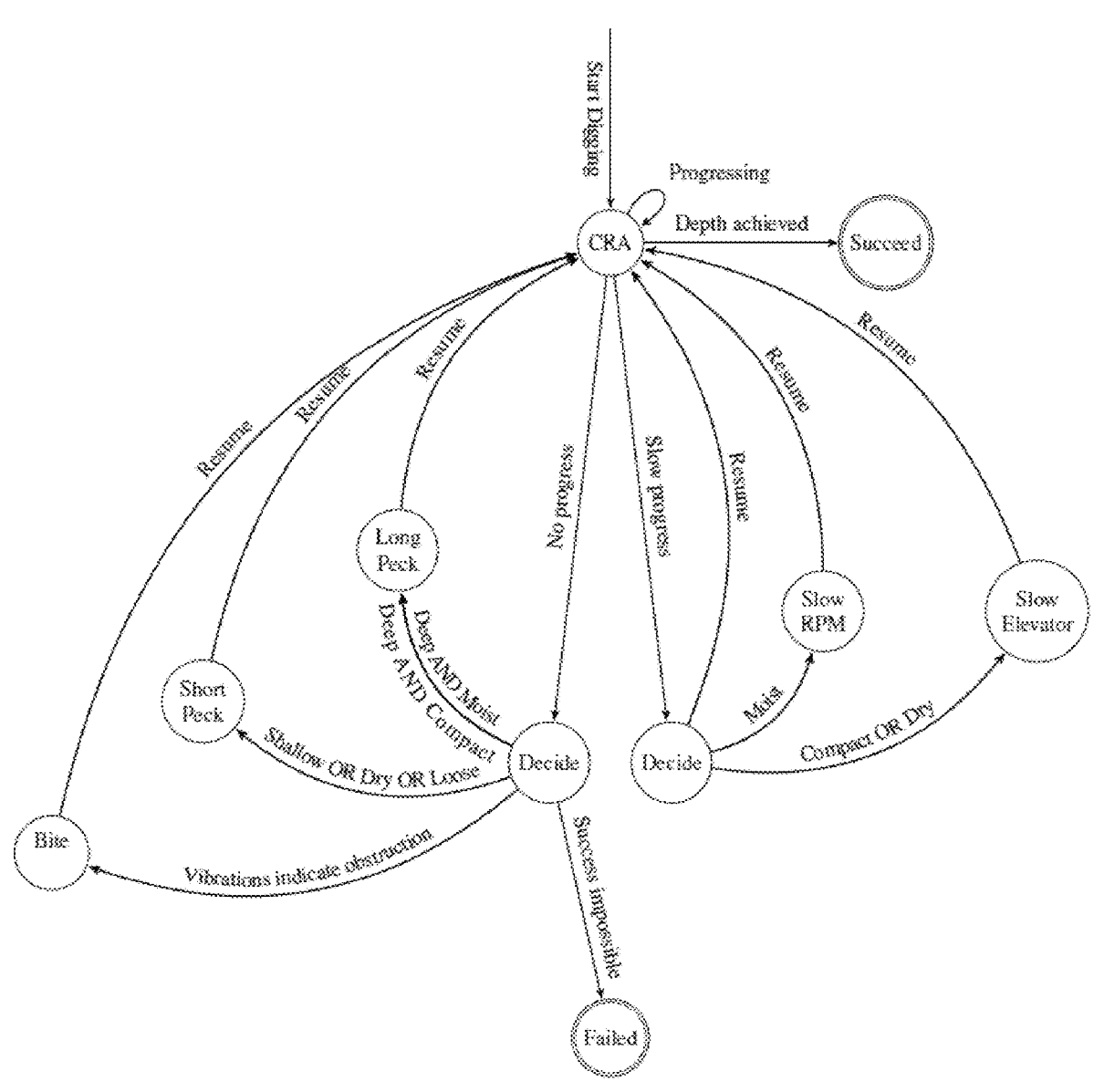
FIG. 8 is a state diagram for an example state machine for adaptive auger driving based on soil classification.

FIG. 8 is a state diagram for an example state machine for adaptive auger driving based on soil classification. As shown in FIG. 8, various factors, such as soil conditions and speed of progress and vibrations indicating obstructions, can be used to change the control of the motors for driving the auger into the soil.

Figure 9:
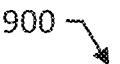
FIG. 9 is a flow diagram of an example method for adaptive mission control based on soil classification values.

FIG. 9 is a flow diagram of an example method 900 for adaptive mission control based on soil classification values. The method 900 can be performed, for example, by the UAS 100 of FIG. 1 having a sensor emplacement system.

The method 900 includes deploying the UAS by controlling a propulsion system of the UAS to land the UAS at a sensor emplacement site (902). The method 900 includes initiating sensor emplacement by controlling one or more motors of the sensor emplacement system to drive an auger into soil at the sensor emplacement site (904).

The method 900 includes measuring one or more augering parameters from the sensor emplacement system and determining, using a classifier trained on soil data and augering data, one or more soil classification values for the soil based on the one or more augering parameters (906). The method 900 includes determining a probability of success in emplacing the sensor at the site based on the soil classification values (908).

The method 900 can include, for example, sending the probability to a remote operator or autonomously altering the mission based on the probability of success. The method 900 can include determining whether the probability exceeds a threshold (910) and, if so, continue to drive the auger into the soil. If not, the method 900 includes selecting an alternate site or ending the mission (912).

An emplacement may fail, for example, if the soil is too compact or has extraneous obstructions (e.g. roots, rocks), or the sensor may get stuck or partially emplaced. If these situations can be accurately detected early, the UAS can extract the sensor and try an alternate location. Setting a time limit on a digging attempt provides an easy litmus test but can lead to either wasting resources on what will be an unsuccessful dig, or aborting a potentially successful dig and subsequently wasting energy flying to a new location. In either case, faster, more reliable prediction will yield improved emplacement results. To illustrate, in some trials that were conducted, 29% of attempts succeed within 20 seconds, but of those that go longer there is a significant variance in the time it takes to succeed, and only 48% fail to reach the target depth.

Success in emplacement is best characterized as a stochastic event. Although knowing the soil type can reduce uncertainty, the likelihood of unforeseen obstructions slowing or stopping the progress is high and difficult to predict. Nonetheless, the UAV can be configured with a decision-making algorithm for a digging UAS that enables autonomous monitoring of digging to quickly decide if success is likely or if another digging location should be selected. Markov Decision Processes (MDP) provide optimal decision-making under uncertainty, and as such, the UAV can be configured with an MDP to predict the outcome of a single digging event. Alternatively, the UAV can use binary decision trees or a support vector machine or other appropriate classification technique.

A MDP is a tuple representing states, actions, transition probabilities, rewards, and a discount factor, respectively. The MDP can be solved to generate an optimal policy, representing which action should be taken in any state. For digging success prediction, the transitions between states are highly uncertain, sometimes being equi-probabilistically distributed among 3-4 outgoing transitions from a state. Moreover, numerous ending states may be present, with numerous paths to those states. This uncertainty stems from the soil, what may be in the soil, the failure conditions of the motor and auger, as well as how well a particular auger performs in a particular soil type. This uncertainty is well represented by a MDP.

The MDP can include various states and actions, which can be either: 1) continue digging or 2) stop digging. Transition probabilities can be generated from training trials. A reward table can be created from training data. Rewards can be increased to encourage stopping when a successful outcome seemed unlikely. This includes situations where very little digging depth is achieved over a fixed period of time, or when the system was in a state where high motor current draw and low motor RPM indicated a potential stall situation.

States in which the system had achieved its target depth were considered termination states and were assigned the largest reward for the stopping action. To encourage continuation, higher rewards can be assigned if a positive rate of digging progress was observed, or the system had been digging only a short time. To further tune the MDP reward table, the initial MDP-generated policy can be run against random successful and unsuccessful digs observing the MDP's "decision" at each time interval within the files. This allows areas within our reward table to be adjusted to increase the chance of the policy leading to a successful outcome.

Various combinations and sub-combinations of the structures and features described in this specification are contemplated and will be apparent to a skilled person having knowledge of this disclosure. Any of the various features and elements as disclosed in this specification may be combined with one or more other disclosed features and elements unless indicated to the contrary.

Correspondingly, the subject matter as claimed is intended to be broadly construed and interpreted, as including all such variations, modifications and alternative embodiments, within its scope and including equivalents of the claims. It is understood that various details of the presently disclosed subject matter may be changed without departing from the scope of the claims. Furthermore, the foregoing description is for the purpose of illustration only, and not for the purpose of limitation.

What is claimed is:

1. An unmanned aircraft system (UAS) comprising:
a propulsion system;
a sensor;
a sensor emplacement system comprising an auger and one or more motors; and
a control system comprising at least one processor and configured for:
controlling the propulsion system to land the UAS at a sensor emplacement site;
controlling the one or more motors of the sensor emplacement system to drive the auger into soil at the sensor emplacement site;
measuring one or more augering parameters from the sensor emplacement system while driving the auger into the soil;
determining, using an autonomous system trained on soil data and augering data, one or more soil classification values for the soil based on the one or more augering parameters; and
completing, using the soil classification values, an emplacement of the sensor into the soil.

2. The UAS of claim 1, wherein the one or more augering parameters comprise one or more of:
revolutions per minute of an auger motor causing the auger to rotate;
current draw of the auger motor;
weight on auger bit as measured by a strain gauge of the sensor emplacement system;
elevator position of an elevator system driving the auger downward into the soil; and
acceleration in an X axis, a Y axis, and/or a Z axis.

3. The UAS of claim 1, wherein the one or more soil classification values comprise one or more of: soil moisture and soil compressive strength.

4. The UAS of claim 1, wherein the autonomous system comprises a classifier and is trained on the soil data and the augering data using one of the following machine learning models:
decision tree;
linear discriminant;
naïve Bayes;
k-nearest neighbor; and
Gaussian process.

5. The UAS of claim 1, wherein the control system is configured for selecting a first digging profile for controlling the one or more motors of the sensor emplacement system and, after initially driving the auger into the soil, selecting a second digging profile based on the one or more soil classification values.

6. The UAS of claim 5, wherein selecting the second digging profile based on the one or more soil classification values comprises one of:

adjusting a length of a pecking movement;

slowing revolutions per minute of an auger motor causing the auger to rotate; and slowing a speed of an elevator system driving the auger downward into the soil.

7. The UAS of claim 1, wherein the control system is configured for determining, using the one or more soil classification values, a probability of success in emplacing a sensor into the soil at the sensor emplacement site.

8. A method performed on an unmanned aircraft system (UAS), the method comprising:

controlling one or more motors of a sensor emplacement system to drive an auger into soil at a sensor emplacement site;

measuring one or more augering parameters from the sensor emplacement system while driving the auger into the soil;

determining, using an autonomous system trained on soil data and augering data, one or more soil classification values for the soil based on the one or more augering parameters; and completing, using the soil classification values, an emplacement of a sensor into the soil.

9. The method of claim 8, wherein the one or more augering parameters comprise one or more of:

revolutions per minute of an auger motor causing the auger to rotate;

current draw of the auger motor;

weight on auger bit as measured by a strain gauge of the sensor emplacement system;

elevator position of an elevator system driving the auger downward into the soil; and acceleration in an X axis, a Y axis, and/or a Z axis.

10. The method of claim 8, wherein the one or more soil classification values comprise one or more of: soil moisture and soil compressive strength.

11. The method of claim 8, wherein the autonomous system comprises a classifier and is trained on the soil data and the augering data using one of the following machine learning models:

decision tree;

linear discriminant;

naïve Bayes;

k-nearest neighbor; and

Gaussian process.

12. The method of claim 8, wherein the control system is configured for selecting a first digging profile for controlling the one or more motors of the sensor emplacement system and, after initially driving the auger into the soil, selecting a second digging profile based on the one or more soil classification values.

13. The method of claim 12, wherein selecting the second digging profile based on the one or more soil classification values comprises one of:

adjusting a length of a pecking movement;

slowing revolutions per minute of an auger motor causing the auger to rotate; and slowing a speed of an elevator system driving the auger downward into the soil.

14. The method of claim 8, wherein the control system is configured for determining, using the one or more soil classification values, a probability of success in emplacing a sensor into the soil at the sensor emplacement site.

15. A sensor emplacement system for deployment on an unmanned aircraft system (UAS), the sensor emplacement system comprising:

an auger;

a sensor;

one or more motors; and a control system comprising at least one processor and configured for:

controlling the one or more motors to drive the auger into soil at a sensor emplacement site;

measuring one or more augering parameters during driving the auger into the soil;

determining, using an autonomous system trained on soil data and augering data, one or more soil classification values for the soil based on the one or more augering parameters; and completing, using the soil classification values, an emplacement of the sensor into the soil.

16. The sensor emplacement system of claim 15, wherein the one or more augering parameters comprise one or more of:

revolutions per minute of an auger motor causing the auger to rotate;

current draw of the auger motor;

weight on auger bit as measured by a strain gauge of the sensor emplacement system;

elevator position of an elevator system driving the auger downward into the soil; and acceleration in an X axis, a Y axis, and/or a Z axis.

17. The sensor emplacement system of claim 15, wherein the one or more soil classification values comprise one or more of: soil moisture and soil compressive strength.

18. The sensor emplacement system of claim 15, wherein the autonomous system comprises a classifier and is trained on the soil data and the augering data using one of the following machine learning models:

decision tree;

linear discriminant;

naïve Bayes;

k-nearest neighbor; and

Gaussian process.

19. The sensor emplacement system of claim 15, wherein the control system is configured for selecting a first digging profile for controlling the one or more motors of the sensor emplacement system and, after initially driving the auger into the soil, selecting a second digging profile based on the one or more soil classification values.

20. The sensor emplacement system of claim 19, wherein selecting the second digging profile based on the one or more soil classification values comprises one of:

adjusting a length of a pecking movement;

slowing revolutions per minute of an auger motor causing the auger to rotate; and slowing a speed of an elevator system driving the auger downward into the soil.

21. A sensor emplacement system for deployment on an unmanned aircraft system (UAS), the sensor emplacement system comprising:

an auger;

a sensor;

one or more motors; and a control system comprising at least one processor and configured for:

controlling the one or more motors to drive the auger into emplacement material at a sensor emplacement site;

measuring one or more augering parameters while driving the auger into the emplacement material;

determining, using an autonomous system trained on data from an augering process and emplacement material, one or more emplacement material classification values for the emplacement material based on the one or more augering parameters; and completing, using the emplacement material classification values, an emplacement of the sensor into the emplacement material.

22. The sensor emplacement system of claim 21, wherein the one or more augering parameters comprise one or more of:

revolutions per minute of an auger motor causing the auger to rotate;

current draw of the auger motor;

weight on auger bit as measured by a strain gauge of the sensor emplacement system;

elevator position of an elevator system driving the auger downward into the soil; and acceleration in an X axis, a Y axis, and/or a Z axis.

23. The sensor emplacement system of claim 21, wherein the emplacement material comprises wood, metal, concrete, or ice.

* * * * *